US009141758B2

(12) United States Patent
Kress et al.

(10) Patent No.: US 9,141,758 B2
(45) Date of Patent: Sep. 22, 2015

(54) SYSTEM AND METHOD FOR ENCRYPTING PROVIDER IDENTIFIERS ON MEDICAL SERVICE CLAIM TRANSACTIONS

(75) Inventors: Andrew E. Kress, Gladwyne, PA (US); Steve E. Stevens, Chalfont, PA (US); Ann R. Martin, Philadelphia, PA (US)

(73) Assignee: IMS Health Incorporated, Danbury, CT (US)

( * ) Notice: Subject to any disclaimer, the term of this patent is extended or adjusted under 35 U.S.C. 154(b) by 382 days.

(21) Appl. No.: 12/684,748

(22) Filed: Jan. 8, 2010

(65) Prior Publication Data
US 2010/0217973 A1     Aug. 26, 2010

Related U.S. Application Data

(60) Provisional application No. 61/154,062, filed on Feb. 20, 2009.

(51) Int. Cl.
G06F 21/00     (2013.01)
G06F 19/00     (2011.01)
G06F 17/30     (2006.01)
G06F 21/62     (2013.01)

(52) U.S. Cl.
CPC ............. *G06F 19/328* (2013.01); *G06F 17/30* (2013.01); *G06F 21/6254* (2013.01); *G06F 19/322* (2013.01)

(58) Field of Classification Search
CPC . G06F 21/6254; G06F 19/328; G06F 19/322; G06F 17/30; G06F 21/6227
USPC ........... 713/150–181, 277, 189; 709/201–203
See application file for complete search history.

(56) References Cited

U.S. PATENT DOCUMENTS

| 3,752,904 A | 8/1973 | Waterbury |
| 3,896,266 A | 7/1975 | Waterbury |
| 4,979,832 A | 12/1990 | Ritter |

(Continued)

FOREIGN PATENT DOCUMENTS

| EP | 0869637 A2 | 10/1998 |
| EP | 1026603 A2 | 8/2000 |

(Continued)

OTHER PUBLICATIONS

"Electronic Medical Record Systems and Databases" (May 15, 2001) by Shixin Zhang and C. Forbes Dewey, Jr.; 33 pages; converted to PDF originally from http://icmit.mit.edu/sxzhang/healthcare/word.htm.*

(Continued)

*Primary Examiner* — Chau Le
*Assistant Examiner* — Don Zhao
(74) *Attorney, Agent, or Firm* — Fish & Richardson P.C.

(57) ABSTRACT

The present invention relates to a method and a system for collecting and providing reports of activities of medical service providers, while encrypting confidential information. Specifically, the present invention provides systems and methods for collecting and providing information from medical claim transactions without information for specifically identifying the particular medical service provider. The present invention also allows for correlation of medical claim transactions with providers' information without using information that can be used to specifically identify the particular medical service provider (provider identifier).

19 Claims, 11 Drawing Sheets

(56) References Cited

U.S. PATENT DOCUMENTS

| | | | |
|---|---|---|---|
| 4,993,068 A | 2/1991 | Piosenka et al. | |
| 5,003,539 A | 3/1991 | Takemoto et al. | |
| 5,005,200 A | 4/1991 | Fischer | |
| 5,070,452 A | 12/1991 | Doyle, Jr. et al. | |
| 5,214,702 A | 5/1993 | Fischer | |
| 5,299,121 A | 3/1994 | Brill et al. | |
| 5,301,105 A | 4/1994 | Cummings, Jr. | |
| 5,371,797 A | 12/1994 | Bocinsky, Jr. | |
| 5,471,382 A | 11/1995 | Tallman et al. | |
| 5,502,764 A | 3/1996 | Naccache | |
| 5,581,749 A | 12/1996 | Hossain et al. | |
| 5,606,610 A | 2/1997 | Johansson | |
| 5,644,778 A | 7/1997 | Burks et al. | |
| 5,652,842 A | 7/1997 | Siegrist, Jr. et al. | |
| 5,664,109 A | 9/1997 | Johnson et al. | |
| 5,666,492 A | 9/1997 | Rhodes et al. | |
| 5,704,044 A | 12/1997 | Tarter et al. | |
| 5,724,575 A | 3/1998 | Hoover et al. | |
| 5,754,938 A | 5/1998 | Herz et al. | |
| 5,758,085 A | 5/1998 | Kouoheris et al. | |
| 5,758,095 A | 5/1998 | Albaum et al. | |
| 5,787,186 A | 7/1998 | Schroeder | |
| 5,793,969 A | 8/1998 | Kamentsky et al. | |
| 5,799,086 A | 8/1998 | Sudia | |
| 5,799,308 A | 8/1998 | Dixon | |
| 5,821,871 A | 10/1998 | Benzler | |
| 5,823,948 A | 10/1998 | Ross, Jr. et al. | |
| 5,825,906 A | 10/1998 | Obata et al. | |
| 5,832,449 A | 11/1998 | Cunningham | |
| 5,867,821 A | 2/1999 | Ballantyne et al. | |
| 5,876,926 A | 3/1999 | Beecham | |
| 5,890,129 A | 3/1999 | Spurgeon | |
| 5,907,677 A | 5/1999 | Glenn et al. | |
| 5,915,240 A | 6/1999 | Karpf | |
| 5,918,208 A | 6/1999 | Javitt | |
| 5,920,854 A | 7/1999 | Kirsch et al. | |
| 5,926,810 A | 7/1999 | Noble et al. | |
| 5,956,716 A | 9/1999 | Kenner et al. | |
| 5,961,593 A | 10/1999 | Gabber et al. | |
| 5,970,462 A | 10/1999 | Reichert | |
| 5,991,731 A | 11/1999 | Colon et al. | |
| 5,995,939 A | 11/1999 | Berman et al. | |
| 6,003,006 A | 12/1999 | Colella et al. | |
| 6,012,051 A | 1/2000 | Sammon, Jr. et al. | |
| 6,014,631 A | 1/2000 | Teagarden et al. | |
| 6,018,713 A | 1/2000 | Coli et al. | |
| 6,024,287 A | 2/2000 | Takai et al. | |
| 6,079,021 A | 6/2000 | Abadi et al. | |
| 6,085,322 A | 7/2000 | Romney et al. | |
| 6,249,768 B1 | 6/2001 | Tulskie, Jr. et al. | |
| 6,266,675 B1 | 7/2001 | Evans et al. | |
| 6,302,844 B1 | 10/2001 | Walker et al. | |
| 6,317,700 B1 | 11/2001 | Bagne | |
| 6,341,267 B1 | 1/2002 | Taub | |
| 6,397,224 B1 | 5/2002 | Zubeldia et al. | |
| 6,421,650 B1 | 7/2002 | Goetz et al. | |
| 6,449,621 B1 | 9/2002 | Pettovello | |
| 6,496,931 B1 | 12/2002 | Rajchel et al. | |
| 6,654,724 B1 | 11/2003 | Rubin et al. | |
| 6,732,113 B1 | 5/2004 | Ober et al. | |
| 6,734,886 B1 | 5/2004 | Hagan et al. | |
| 6,874,085 B1* | 3/2005 | Koo et al. | 713/165 |
| 6,915,265 B1 | 7/2005 | Johnson | |
| 7,184,947 B2 | 2/2007 | Matsuoka et al. | |
| 7,200,578 B2 | 4/2007 | Paltenghe et al. | |
| 7,309,001 B2 | 12/2007 | Banfield et al. | |
| 7,376,677 B2 | 5/2008 | Ober et al. | |
| 7,386,526 B1 | 6/2008 | Chappel | |
| 7,823,207 B2* | 10/2010 | Evenhaim | 726/26 |
| 8,121,868 B1* | 2/2012 | Grady et al. | 705/3 |
| 8,131,646 B2* | 3/2012 | Kocher et al. | 705/54 |
| 8,374,888 B2* | 2/2013 | Earles et al. | 705/2 |
| 2002/0002474 A1* | 1/2002 | Michelson et al. | 705/3 |
| 2002/0143434 A1* | 10/2002 | Greeven et al. | 700/236 |
| 2002/0198473 A1 | 12/2002 | Kumar et al. | |
| 2003/0097358 A1 | 5/2003 | Mendez | |
| 2004/0199781 A1 | 10/2004 | Erickson et al. | |
| 2004/0215981 A1 | 10/2004 | Ricciardi et al. | |
| 2005/0027564 A1 | 2/2005 | Yantis | |
| 2005/0065824 A1* | 3/2005 | Kohan | 705/3 |
| 2005/0065912 A1 | 3/2005 | Cafrelli et al. | |
| 2005/0165623 A1 | 7/2005 | Landi et al. | |
| 2005/0234740 A1 | 10/2005 | Krishnan et al. | |
| 2005/0236474 A1 | 10/2005 | Onuma et al. | |
| 2005/0256740 A1 | 11/2005 | Kohan et al. | |
| 2005/0256741 A1 | 11/2005 | Kohan et al. | |
| 2005/0256742 A1 | 11/2005 | Kohan et al. | |
| 2005/0268094 A1* | 12/2005 | Kohan et al. | 713/165 |
| 2006/0020611 A1* | 1/2006 | Gilbert et al. | 707/100 |
| 2006/0026156 A1 | 2/2006 | Zuleba | |
| 2006/0288095 A1* | 12/2006 | Torok et al. | 709/223 |
| 2007/0100595 A1* | 5/2007 | Earles et al. | 703/13 |
| 2008/0059227 A1* | 3/2008 | Clapp | 705/2 |
| 2008/0076971 A1* | 3/2008 | Clapp | 600/300 |
| 2008/0091474 A1 | 4/2008 | Ober et al. | |
| 2008/0120296 A1* | 5/2008 | Kariathungal et al. | 707/6 |
| 2008/0133273 A1* | 6/2008 | Marshall | 705/3 |
| 2008/0137848 A1* | 6/2008 | Kocher et al. | 380/201 |
| 2008/0147554 A1 | 6/2008 | Stevens et al. | |
| 2009/0198519 A1* | 8/2009 | McNamar | 705/3 |
| 2010/0027780 A1* | 2/2010 | Jung et al. | 380/28 |
| 2010/0114607 A1 | 5/2010 | Kress et al. | |
| 2010/0217973 A1 | 8/2010 | Kress et al. | |
| 2013/0018727 A1* | 1/2013 | Earles et al. | 705/14.49 |

FOREIGN PATENT DOCUMENTS

| | | |
|---|---|---|
| JP | 6083847 A | 3/1994 |
| JP | 10021302 A | 1/1998 |
| WO | WO-9515628 A1 | 6/1995 |
| WO | WO-9641275 A1 | 12/1996 |
| WO | WO-9642059 A1 | 12/1996 |
| WO | WO-0077642 A1 | 12/2000 |
| WO | WO-0118631 A1 | 3/2001 |

OTHER PUBLICATIONS

"Selecting a database encryption solution" (Mar. 31, 2008) by Ulf Mattsson; 5 pages; converted to PDF originally from http://it.toolbox.com/wiki/index.php/Selecting_a_database_encryption_solution.*

U.S. Patent and Trademark Office, Office Action for U.S. Appl. No. 09/665,752, May 5, 2004, 5 pgs.

U.S. Patent and Trademark Office, Office Action for U.S. Appl. No. 09/665,752, Mar. 4, 2005, 6 pgs.

U.S. Patent and Trademark Officer, Office Action for U.S. Appl. No. 09/665,752, Dec. 16, 2005, 4 pgs.

U.S. Patent and Trademark Office, Office Action for U.S. Appl. No. 09/665,752, Mar. 16, 2007, 7 pgs.

U.S. Patent and Trademark Office, Office Action for U.S. Appl. No. 09/665,752, Jan. 25, 2008, 7 pgs.

U.S. Patent and Trademark Office, Office Action for U.S. Appl. No. 09/665,752, Dec. 8, 2008, 8 pgs.

J.D. Halamka, P. Szolovits, D. Rind, and C. Safran, A WWW Implementation of National Recommendations for Protecting Electronic Health Information, Journal of the American Medical Informatics Association, vol. 4, No. 6, Nov./Dec. 1997, pp. 458-464.

R. Anderson, The DeCODE Proposal for an Icelandic Health Database, Oct. 20, 1998, pp. 1-12, www.decode.is.

H. Bouzelat, C. Quantin and L. Dusserre, Extraction and Ananymity Protocol of Medical File, Proceedings of the American Medical Informatics Association Annual Fall Symposium, 1996, pp. 323-327, AMIA, Inc.

K.R. Iversen and T.O. Grotan, Socio-technical aspects of the use of health related personal information for management and research, International journal of Bio-Medical Computing, vol. 43, 1996, pp. 83-91, Elsevier Science Ireland Ltd.

A. Ohrn and L. Ohno-Machado, Using Boolean reasoning to ananymize databases, Artificial Intelligence in Medicine, vol. 15, 1999, pp. 235-254, Elsevier Science B.V.

K. Kahl, G. Dickson, J. Kebisek and M. Powell, Bar code tracking

(56) References Cited

OTHER PUBLICATIONS system enhances record- and film-handling productivity, Top Health Rec Manage, vol. 12, No. 3, Mar. 1992, 1 pg., St. Joseph's Hospital, Milwaukee, WI, PubMed—indexed for MEDLINE.

E.T. Carroll, S. Wright, C. Zakoworotny, Securely Implementing Remote Access within Health Information Management, Journal of AHIMA, vol. 69, No. 3, Mar. 1998, pp. 46-49, copied from the National Library of Medicine.

F. Scheuren and P. Baier, HIPAA Certification for SDI's De-Identification Technology, Jun. 4, 2007, pp. 1-24, Washington, DC.

English Translation of Japanese Office Action for co-pending application, Reference No. B025547, Mailing No. 571403, Mailing Date: Aug. 10, 2010, Patent Application No. 2001-525614.

S. Chaudhuri, et al: An overview of Data Warehousing and OLAP Technology, Sigmod Record, Sigmod, New York, NY, US, vol. 26, No. 1, Mar. 199, (Mar. 1997), pp. 65-74, XP002193792, ISSN: 0163-5808.

V.M. Brannigan and B. R. Beier, Patient privacy in the era of medical computer networks: a new paradigm for a new technology, Proceedings of the Eighth World Congress on Medical Informatics, vol. 8, No. 8, Jul. 23, 1995, Jul. 27, 1995, pp. 640-643, XP009040274, Vancouver, British Columbia, Canada, ISSN: 1569-6332.

C. Quantin, et al. How to ensure data security of an epidemiological follow up: quality assessment of an anonymous record linkage procedure, International Journal of Medical Informatics, Elsevier Scientific Publishers, Shannon, IR, vol. 49, No. 1, Mar. 1998, pp. 117-122, XP004149470, ISSN: 1386-5056.

R. J. Anderson, A security policy model for clinical information systems, Security and Privacy, 1996, Proceedings, 1996 IEEE Symposium on Oakland, CA, USA May 6-8, 1996 (May 6, 1996), pp. 30-43, XP010164923, ISBN: 0/8186-7417-2.

Supplementary European Search Report of EP 00 96 5216.

International Search Report of PCT/US00/25818.

Secure Hash Standard, National Institute of Standards and Technology, Aug. 1, 2002, pp. i-iv and 1-79, Federal Information Processing Standards Publication 180-2 (+Change Notice to include SHA-224).

Why Clearinghouses Transmit Electronic Claims to Insurance Carriers, and Why the Service They Provide is Essential to Medical Practices, Electronic Claim Clearinghouses, MPM Soft, Practice Billing Software, pp. 1-7, www.mpmsoft.com/EDI/clearinghouse. htm, printed Jan. 5, 2009.

* cited by examiner

| DATE OF SERVICE | PRODUCT / SERVICE ID | SERVICE PROVIDER (PHARMACY) ID | PRESCRIPTION / SERVICE REFERENCE NUMBER | PRESCRIBER_ID | MORE NCPDP PRESCRIPTION FIELDS... |
|---|---|---|---|---|---|
| 12/25/2008 | 00093723401 | 8138105467 | 6804554 | BM1477974 | |
| 12/25/2008 | 63653117105 | 5347776 | 7621414 | 1790903580 | |
| 12/25/2008 | 00169183311 | 8643140106 | 0729681 | 1437135689 | |
| 12/25/2008 | 62856024330 | 8673491583 | 6309050 | BC5689975 | |
| 12/25/2008 | 00406035705 | 8673491578 | 4516020 | 1578548831 | |
| 12/25/2008 | 00186504031 | 8673491584 | 6317734 | 1215125322 | |
| 12/25/2008 | 00002323704 | 8683521034 | 341206 | 1063520691 | |
| 12/25/2008 | 52544029128 | 8865340261 | 4721169 | BV6423607 | |
| 12/25/2008 | 00085113201 | 8865340252 | 4788026 | BL5848622 | |
| 12/25/2008 | 00186037220 | 8865340262 | 4784924 | MG1349060 | |
| 12/25/2008 | 00781518710 | 8714833560 | 1277898 | 1669552484 | |
| 12/25/2008 | 00597005801 | 8673585050 | 1116121 | 1629180758 | |
| 12/25/2008 | 00172208380 | 8673585037 | 1117946 | 1386722709 | |
| 12/25/2008 | 00172208380 | 8673585051 | 1108811 | 1568457225 | |
| 12/25/2008 | 00069422066 | 8693611936 | 6899908 | 1578584958 | |
| 12/25/2008 | 64980011201 | 8734144702 | 1493697 | BA8881370 | |
| 12/25/2008 | 63653117105 | 8734144785 | 1486372 | AM2690561 | |
| 12/25/2008 | 00173069600 | 8784697135 | 1094680 | 1295719723 | |
| 12/25/2008 | 58177029304 | 8714963247 | 6910922 | 1902963654 | |
| 12/25/2008 | 00228222196 | 8714963249 | 6921500 | BT4004471 | |
| 12/25/2008 | 53489010701 | 8714963246 | 6918973 | AK6692288 | |
| 12/25/2008 | 00378638001 | 8693612464 | 6780679 | 1669470663 | |
| 12/25/2008 | 00378021610 | 8693612467 | 6793600 | 1033156618 | |
| 12/25/2008 | 00378477501 | 8693612455 | 6901001 | 1497727532 | |
| 12/25/2008 | 00603258221 | 8754394111 | 0103206 | 1548233082 | |
| 12/25/2008 | 58177020204 | 8643140103 | 0740333 | 1437135689 | |
| 12/25/2008 | 00046110281 | 8643140113 | 0718081 | 1437135689 | |
| 12/25/2008 | 62584097590 | 3947556 | 3525266 | 1356320981 | |
| 12/25/2008 | 63653117105 | 3947567 | 3367539 | 1588639123 | |
| 12/25/2008 | 00008083721 | 8683521030 | 338710 | 1417070534 | |

MORE NCPDP PRESCRIPTION TRANSACTIONS...

FIG. 2

| DATE OF SERVICE | PRODUCT / SERVICE ID | SERVICE PROVIDER (PHARMACY) ID | PRESCRIPTION / SERVICE REFERENCE NUMBER | PRESCRIBER_ID ENCRYPTED | MORE NCPDP PRESCRIPTION FIELDS... |
|---|---|---|---|---|---|
| 12/25/2008 | 00093723401 | 8138105467 | 6804554 | aZŒ¬ÊþÝr¯YtÈñ 75Ý Ä{] Ü™JìÝ | |
| 12/25/2008 | 63653117105 | 5347776 | 7621414 | Q&Ì ŠÙ.íZþÚäā-о̄ ₤'@§û/í6 ?î,çþ | |
| 12/25/2008 | 00169183311 | 8643140106 | 0729681 | ½}Ü:ÝþíhÄ¶*g™X} ^RÕÁ:aŸyōÜ4o | |
| 12/25/2008 | 62856024330 | 8673491583 | 6309050 | v.èñÖä'¼XB_°¨f-¡,¼ JÖg´Wåó7 ™©± | |
| 12/25/2008 | 00406035705 | 8673491578 | 4516020 | PÒ&±ÇQ#™Yv X«HÕNäy÷.™ï0l ³ïµS_ | |
| 12/25/2008 | 00186504031 | 8673491584 | 6317734 | á#gf ,#×X úóô Êwèʻ L /ÞC6èA | |
| 12/25/2008 | 00002323704 | 8683521034 | 341206 | ®D e6Á+%Èà˙ þŸe²;±ſ˙Øly ō/•Â W³#k | |
| 12/25/2008 | 52544029128 | 8865340261 | 4721169 | Î\)Á úí2ùGj1,‰Å֥bÒØg ~Çſ†Ô !" | |
| 12/25/2008 | 00085113201 | 8865340252 | 4788026 | 7,7N«š9\0lQ Ý<,l 9Ç_Côo¼°?èi | |
| 12/25/2008 | 00186037220 | 8865340262 | 4784924 | äví¢ 1ý© iwi{i»É9Ë¨ '»>ìU°¼ | |
| 12/25/2008 | 00781518710 | 8714833560 | 1277898 | c08òż, ý*/ · | |
| 12/25/2008 | 00597005801 | 8673585050 | 1116121 | Iýz#˙0 »Òi Á)... °°ÎKB¿Í¼ 5¢Á¢BÓÃ¨¨ | |
| 12/25/2008 | 00172208380 | 8673585037 | 1117946 | 'µ'+:, ýRwÁlùœì $Š¡ýDR®ž"_ | |
| 12/25/2008 | 00172208380 | 8673585051 | 1108811 | qì©ª> -"Ú>VtPï ò_¨Tt«Öé¨oJŠ^Cè<À | |

FIG. 3(a)

| | | | | |
|---|---|---|---|---|
| 12/25/2008 | 00069422066 | 8693611936 | 6899908 | w□4dõÀ□âXÿ)V¦<br>wÍ¦+#G□Ä□ZÒíB¤Œfh |
| 12/25/2008 | 64980011201 | 8734144702 | 1493697 | p™<br>ã]®<br>$Ò□Ë[JÚr□pVï□ıÑÜïŽÜüè fi |
| 12/25/2008 | 63653117105 | 8734144785 | 1486372 | u□£#.Ùw`□□aδ™Á} |
| 12/25/2008 | 00173069600 | 8784697135 | 1094680 | □nx]‹½'?µ□mß'Í□s+□WœÖ·á'n<br>5!ì–ŒX |
| 12/25/2008 | 58177029304 | 8714963247 | 6910922 | ´d¯T›□€:ú?þNó;U¾ÙŠïÜ□ÜyF¼ì□ □ù□pÒ |
| 12/25/2008 | 00228222196 | 8714963249 | 6921500 | ÒxœP□ □□}Ç□ñdll!ô□ □èò1□ü¼-‡;¤□èÚ+ |
| 12/25/2008 | 53489010701 | 8714963246 | 6918973 | Y.(;®õß□□·¦×Uw6Ù.n*§vÀMÂ'üoü290ì· |
| 12/25/2008 | 00378638001 | 8693612464 | 6780679 | *ë]°GÝ=$tÚ6□`Ù—Fô1›ëä4□A©K4œ¦„[qA |
| 12/25/2008 | 00378021610 | 8693612467 | 6793600 | ƒûì¿Ï®'§ɴhÈ‰Hâ£ûlj®ô²„ÉÂh¶U□ô¯N |
| 12/25/2008 | 00378477501 | 8693612455 | 6901001 | –o□áN□÷‡jLT∂□Èm}£ÄÒ ¦$□èþoüRǏ□<¯ |
| 12/25/2008 | 00603258221 | 8754394111 | 0103206 | Ë□_□M□`3'õÖ\xÌþ^-□Č`pŒÒñ5üíA¥Õ□ |
| 12/25/2008 | 58177020204 | 8643140103 | 0740333 | □½}□Ù:Ýþ¦hÃ¢*□g™X}<br>^RÔA:aÝy□δÜ4o |
| 12/25/2008 | 00046110281 | 8643140113 | 0718081 | □½}□Ù:Ýþ¦hÃ¢*□g™X}<br>^RÔA:aÝy□δÜ4o |
| 12/25/2008 | 62584097590 | 3947556 | 3525266 | «A<br>ƒ•P?ÆiêEź¬□4□p□µ·Ɓ81□ŒÂu□c<br>?ß |
| 12/25/2008 | 63653117105 | 3947567 | 3367539 | ®Lãä+@/}ꝗXNP□Ë5é3Ñœ°{«ïL□n^`□ŸÖ‰ |
| 12/25/2008 | 00008083721 | 8683521030 | 338710 | â7ÆXB~-8c«)Úpä ±2.<br>{¢a ½□o®µû<"¿O |

MORE NCPDP PRESCRIPTION TRANSACTIONS...

FIG. 3(b)

| ANONYMOUS PRACTITIONER KEY | PRESCRIBER ID |
|---|---|
| 1588 | 1437135689 |
| 67070 | 1417070534 |
| 350935 | 1588639123 |
| 393582 | BL5848622 |
| 457374 | 1033156616 |
| 496104 | 1578548831 |
| 502949 | 1215125322 |
| 517027 | BV6423607 |
| 569365 | 1548233082 |
| 576561 | AM2690561 |
| 626053 | 1578584958 |
| 634891 | AK6692288 |
| 637501 | BT4004471 |
| 641424 | BM1477974 |
| 770012 | BC5689975 |
| 811725 | 1902963654 |
| 853857 | BA8881370 |
| 2354804 | 1790903580 |
| 2439359 | MG1349060 |
| 2873061 | 1063520691 |
| 3243614 | 1295719723 |
| 3342473 | 1356320981 |
| 3397532 | 1386722709 |
| 3571682 | 1497727532 |
| 3688672 | 1568457225 |
| 3794884 | 1629180758 |
| 3853432 | 1669470663 |
| 3858822 | 1669552484 |
| MORE ANONYMOUS PRACTITIONER KEYS | MORE PRESCRIBER IDS |

FIG. 4

| ANONYMOUS PRACTITIONER KEY | MEDICAL SPECIALTY (AMA) | MEDICAL SPECIALTY (NPPES) | ZIP CODE |
|---|---|---|---|
| 1588 | GS | 208D00000X | 35801 |
| 67070 | CHP | 2084P0800X | 94704 |
| 350935 | IM | 207R00000X | 55901 |
| 393582 | IM | 207R00000X | 14224 |
| 457374 | IM | 207R00000X | 24014 |
| 496104 | NS | 207T00000X | 44510 |
| 502949 | D | 207Q00000X | 44410 |
| 517027 | IM | 207R00000X | 98664 |
| 569365 | US | 207Q00000X | 19301 |
| 576561 | N | | 00725 |
| 626053 | GS | 208800000X | 21117 |
| 634891 | OBG | 207V00000X | 75397 |
| 637501 | IM | 207R00000X | 75601 |
| 641424 | FM | 207Q00000X | 75284 |
| 770012 | FM | | 44446 |
| 811725 | IMG | 207R00000X | 75397 |
| 853857 | PTH | | 00612 |
| 2354804 | IM | 390200000X | 55905 |
| 2439359 | | 363AM0700X | 99507 |
| 2873061 | | 207Q00000X | 95827 |
| 3243614 | | 207Q00000X | 02767 |
| 3342473 | TS | 207RP1001X | 55905 |
| 3397532 | IM | 207R00000X | 02903 |
| 3571682 | FM | 207QG0300X | 24015 |
| 3688672 | IM | 207R00000X | 02828 |
| 3794884 | U | 208800000X | 02852 |
| 3853432 | IM | 207R00000X | 24013 |
| 3858822 | IM | 207RA0000X | 92543 |
| MORE ANONYMOUS PRACTITIONER KEYS | MORE MEDICAL SPECIALTIES | | MORE ZIP CODES |

FIG. 5

| ANONYMOUS PRACTITIONER KEY | PRESCRIBER ID ENCRYPTED |
|---|---|
| 1588 | ⏹½}⏹Ú:Ýp¡hÃ¶*⏹g™X}<br>^RÕÁ:aŸy⏹õÜ4o |
| 67070 | â7ÆXB~-8c«)Úpä ±2<br>{¢ə ½⏹o⏹µû«"¿O |
| 350935 | ®Lǎá+@/ÿXNP⏹Ë5ó3Ñœ°('«îL⏹n^'⏹ŸÖ‰<br>!" |
| 393582 | 7,7N‹îŠ9\0I⏹⏹Ý<,I⏹9Ç_Cóo¼°?èί |
| 457374 | ƒûi¿Ì®ˆ§/hÈ‰HâΣùìj®ò²ˌÈÀh¶U⏹õ¯N |
| 496104 | PÖ&⏹±ÇQ⏹#™Yv<br>X«HÓNäy+,™I⏹I ˢïµS_ |
| 502949 | á#gf⏹ˌ#×X⏹⏹⏹ûóò⏹Êwèo<br>L⏹ƒI⏹þC6èA⏹ |
| 517027 | ñ)Á⏹⏹ú¡2úGⱼI‰AØ¥⏹⏹b⏹ÖØg⏹~Çf^†Ò |
| 569365 | Ë⏹_⏹M⏹'3'öÒ\xÌþ^-⏹®ˉ pŒÒñ5úÍA¥Ö⏹ |
| 576561 | u⏹£#.Ùw¨⏹⏹aő™Â} |
| 626053 | w⏹4dõÅ⏹áXÿ)V¦<br>wÍ¦+#G⏹Å⏹ZÒ¦B¤Œfñ |
| 634891 | Y.(;®óß⏹⏹·¦×Uw6Ù.nˢ§vÀMÂ'ûøū290Ĭ |
| 637501 | Òx∞P⏹⏹⏹)ÇαñdI!!ô⏹⏹ê61⏹ü¼-‡;¤⏹èÜ+ |
| 641424 | aZŒ¬⏹ÊþÝr⏹¯YrÈñ 75Ý⏹⏹⏹"Â{} Ü™JÎ¥ |
| 770012 | v.èñÖâ¼XB_°ˉ1-¡⏹,¼<br>J⏹g'Wàô7⏹⏹ ™©± |
| 811725 | 'ďT›⏹€:ú?þNó;U¼ÙŠìÜ⏹ÜyF¼ì⏹⏹ù⏹pÒ |
| 853857 | p™<br>â] ®<br>$Òò˪JÚr⏹pVí⏹IÑÜIŽÜùè ff |
| 2354804 | Q&Iˉ ŠÙ.īZpÛâá-¤ĺˉ£'@§üƒíó⏹<br>?Í,cþ |
| 2439359 | áνÎÇ⏹<br>1ÿ©⏹<br>iwi{i»⏹É9Ể¯ï⏹*⏹>ÌU°¾ |
| 2873061 | ®D⏹e6Á+%Êâ¯þŸeᵌ:±ˉØ1y⏹õ/·Ā⏹Wª#k |
| 3243614 | ⏹nxk½'?µ⏹mß´Í⏹s+⏹WœÒ·á'n<br>5!í--ŒX |

FIG. 6(a)

|  |  |
|---|---|
| 3342473 | «A<br>f-P?ÆiêEž¬☐4☐p☐µ-ß81☐ŒÂu☐ə<br>?ß |
| 3397532 | ☐☐ªµ'+☐:,<br>ýRwÁ1ùœÌ☐☐$Š¶ÿ☐☐DR®ž"_ |
| 3571682 | —ø☐áN☐+‡jLTð☐Èm)£ÁÒ !§☐èþøäRÌ☐<¯ |
| 3688672 | qi©°>☐-ªÚ›VťPT ò_³Tť‹Öé¨øJŠ^Cè<À |
| 3794884 | Iýz#ˇ0<br>»Ò1☐☐Å)... ☐°°ÏKB¿[¼ 5Ã¢ßÓÄ' |
| 3853432 | ²é]ᵖGÝ=$tÙ6☐Ù—Fò1>ëà4☐A©K4œ¦,[qA |
| 3858822 | e0šOž,☐ý*/ |
| MORE ANONYMOUS PRACTITIONER KEYS | MORE PRESCRIBER IDS ENCRYPTED |

FIG. 6(b)

| DATE OF SERVICE | PRODUCT / SERVICE ID | PRESCRIPTION / SERVICE REFERENCE NUMBER | SERVICE PROVIDER PHARMACY ID | PRESCRIBER ID INCRYPTED | ANONYMOUS PRACTITIONER ID | MEDICAL SPECIALTY (AMA) | MEDICAL SPECIALTY (NPPES) | ZIP CODE | MORE NCPDP PRESCRIPTION FIELDS... |
|---|---|---|---|---|---|---|---|---|---|
| 12/25/2008 | 00093723401 | 8138105467 | 6804554 | aZŒ¬◻ÊþÝr◻¯Yŕɱ 75Ÿ◻◻◻°Ą◻ Ü™Jɩ¥ | 641424 | FM | 207Q00000X | 75284 | |
| 12/25/2008 | 63653117105 | 5347776 | 7621414 | Q&Γ˘Ú.ɪZþÚåå¬◻Γ£'@§û∫Ió ◻ ?Í.cþ | 2354804 | IM | 390200000X | 55905 | |
| 12/25/2008 | 00169183311 | 8643140106 | 0729681 | ◻½)◻Ů:Ýpıh¶*◻g™X) ^ŔÕÁ:åŸy◻ôÜ4◻ | 1588 | GS | 208D00000X | 35801 | |
| 12/25/2008 | 32856024330 | 8673491583 | 6309050 | v.èñÖå¼XB_*′f-ɩ◻.¼ J◻g`Wåð7◻◻™©± | 770012 | FM | | 44446 | |
| 12/25/2008 | 00406035705 | 8673491578 | 4516020 | PÕ&◻±ÇQ◻#™Yv X*HÕŇåy+.™İOI *ɩμS_ | 496104 | NS | 207T00000X | 44510 | |
| 12/25/2008 | 00186504031 | 8673491584 | 6317734 | å#gf◻,#×X◻◻◻ú6ðû◻Êwè◻ L◻ʃɪ◻ÞC6èA◻ | 502949 | D | 207Q00000X | 44410 | |
| 12/25/2008 | 00002323704 | 8683521034 | 341206 | ⊛D◻e6Á+%ÈåˉpŸe²;±Γ∅1y◻ ð/·ǍǫW°#k | 2873061 | | 207Q00000X | 65827 | |

FIG. 7(a)

| | | | | | | | | 98 | |
|---|---|---|---|---|---|---|---|---|---|
| | | | | ñ\Áooúî20G¡l,‰Aø¥oobоÕ | | | | 66 | |
| 12/25/2008 | 52544029128 | 8865340261 | 4721169 | Øgo~Çf^†Ó | 517027 | | IM | 207R00000X | 4 |
| | | | | | | | | 14 | |
| | | | | l¨ 7,7N‹îŠ9\0IQoÝ<,Ìo9Ç_Со¼ | | | | 22 | |
| 12/25/2008 | 00085113201 | 8865340252 | 4788028 | °?è¦ | 393582 | | IM | 207R00000X | 4 |
| | | | | åvÎÇo 1ÿ©о | | | | 99 50 | |
| 12/25/2008 | 00186037220 | 8865340262 | 4784924 | Ìw\{I»оÉ9É¯ïо˙о>ÎU°¾ | 2439359 | | | 363AM0700X | 7 |
| | | | | | | | | 92 54 | |
| 12/25/2008 | 00781518710 | 8714833560 | 1277898 | e0š0ż,oÿ°/ | 3858822 | | IM | 207RA0000X | 3 |
| | | | | ŀÿœ#0 »ÒîooÁ)...o°°ÎKB¿{¼ | | | | 02 85 | |
| 12/25/2008 | 00597005801 | 8673585050 | 1116121 | 5Å¢ßÓÅ` | 3794884 | | U | 208800000X | 2 |
| | | | | | | | | 02 90 | |
| 12/25/2008 | 00172208380 | 8673585037 | 1117946 | оо*µ'+о:, ÿRwÀ1ùœîоо\$Šʶÿоо DR®ž* | 3397532 | | IM | 207R00000X | 3 |

FIG. 7(b)

SYSTEM AND METHOD FOR ENCRYPTING PROVIDER IDENTIFIERS ON MEDICAL SERVICE CLAIM TRANSACTIONS

This application claims priority to U.S. Provisional Patent Application No. 61/154,062, filed Feb. 20, 2009, the entire disclosure of which is incorporated herein by reference.

FIELD OF THE INVENTION

The present invention relates to a method and a system for collecting and providing reports of activities of medical service providers, while encrypting confidential information.

BACKGROUND OF THE INVENTION

In the healthcare system, there are generally patients, providers, and payers. A patient is a person who comes to the provider for diagnoses or treatment of medical conditions. Providers include medical practitioners and professionals (such as dentists, nurse practitioners, physicians, and therapists) as well as medical service facilities (such as private offices, hospitals, and outpatient centers), medical service providers (such as pharmacies and laboratories) and other individuals or companies which provide medical diagnosis and treatment services. Payers are payment organizations which assist patients in paying for the diagnosis and treatment fees, and include privately owned health insurance companies, as well as publicly funded programs including Medicare, and Medicaid.

When a patient visits a provider for a diagnosis or treatment, the patient incurs a service fee. Depending on the patient's health insurance plan, the patient may have to pay a portion of the service fee to the provider, also known as a co-payment. The patient or the provider then fills out a medical insurance claim form and submits it to one or more payers to collect the rest of the service fee.

The payers and other organizations have standardized medical claim forms to help the payers and providers communicate with each other in a uniform manner. An exemplary standardized claim form is shown in U.S. Pat. No. 7,386,526, which is incorporated herein by reference. The sample claim form includes 85 fields for entry of information and codes. For instance, field 1 is used for entry of the provider name, address, and telephone number. Fields 12-16 are used for entry of the patient's personal information, such as name, address, birth date, and gender. Fields 67-81 are used for entry of codes corresponding to the diagnosis and procedure performed by the provider. Field 82 is used for entry of an identification code of the attending physician. Each doctor is identified by a physician identification code, rather than by their name, on the medical claim form. Typically, a third party or a manually created conversion table is used to convert between the identification code and the physician's name because identification codes for physicians are publicly available.

Instead of writing down on the claim form the complete diagnoses or procedures that were performed, the provider can utilize a code corresponding to the respective diagnosis and procedure. Diagnosis and procedure codes are standardized and established by healthcare industry standards groups, such as the National Uniform Billing Committee (NUBC), State Uniform Billing Committee (SUBC), American Medical Association (AMA), and Drug Enforcement Administration (DEA).

There are various diagnosis and procedure coding systems for different fields of medicine, services, and treatments. Each coding system contains thousands of unique diagnosis or procedure codes for providers to use in filling out the medical claim forms. One diagnosis coding system is the International Classification of Disease with Clinical Modifications, 9th Revision (ICD-9 CM, hereinafter "ICD-9"), developed by the World Health Organization. Payers and providers commonly use the ICD-9; codes on medical claim forms to describe diagnoses of symptoms, injuries, diseases, and medical conditions. For example, the ICD-9 code 414.0 would be typically recorded for patients who were diagnosed with the condition of Coronary Atherosclerosis. One procedure coding system is the Current Procedure Terminology (CPT) developed by the AMA. Payers and providers commonly use CPT codes to describe procedures or services that providers may perform on patients. These procedures and services are then subsequently reimbursed by the payer, such as an insurer. For example, on a medical claim form, CPT 31255 code indicates that a provider has performed a surgical nasal or sinus endoscopy on the patient. The DEA also developed a Healthcare Common Procedure Coding System (HCPCS) which is a set of procedure codes based on the CPT codes.

In addition, field 82 requires a physician identification code (rather than the physician's name), and fields 12-20 require patient name, gender and age, and date of service. There can also be fields for hospital affiliation, group practice, and other information. Thus, each medical claim form provides a wide range of information related to the provider's activities.

As the healthcare industry grows, the number of medical claims being submitted has increased tremendously. Because of the voluminous amount of medical claims being submitted daily from a large number of providers, many providers and payers have a difficult time managing the medical claims. As a result, clearinghouses have developed to assist payers and providers in dealing with the claim submission process. The clearinghouses receive medical claim forms from the providers, ensure that the forms are properly completed, and distribute the claim forms to the payers. The clearinghouses also distribute the status of submitted claim forms, such as rejected or accepted, from the payers to the providers. Recently, the processing of claim forms has been enhanced by electronic processing of these claim forms. Approximately 90% of all medical claim forms are processed electronically for payment. Electronic processing is further enhanced by use of standard format medical claim forms, such as those in the ANSI ASC X12N 837 Health Care Claims standard and the National Council for Prescription Drug Programs' Prescription Claim Transaction standard Version 5.1.

An exemplary system for providers to submit medical insurance claims to payers is illustrated in co-pending U.S. patent application Ser. No. 12/481,321, filed Jun. 9, 2009. The system includes providers, medical claim forms, clearinghouses, and payers. The providers submit the claim forms to the clearinghouses by paper or electronically as a file or other suitable format. The clearinghouses collect the claim forms from the providers, and distribute them to the payers. The providers can be physicians who provide diagnoses and treatment procedures for patients. The providers can be affiliated with private physician offices, hospitals, and other types of medical service facilities.

Many companies, such as pharmaceutical and medical device manufacturers and organizations related to medical service, have a great interest in promoting their products and services to specific groups of providers. To promote their products and services effectively, those companies want to target their products not to all providers, but to the most relevant group of providers in a specialized field. Thus, before promotion, a company would want a list of providers, such as physicians who performed particular diagnoses and procedures in the field of medicine that would most need the company's products. The providers on the list would be more likely than others to use or introduce the company's products to their patients. For instance, a manufacturer of a device for measuring blood sugar level may want a list of the top 100 physicians in the country that performed the highest number of diabetes diagnoses and treatments in the previous year. Those physicians are more likely than others to diagnose and treat diabetic patients in the near future and introduce the company's blood-level measuring device to their patients. Moreover, the manufacturer may want the list of the top 100 physicians to be sorted by the total number of diagnoses performed, or by gender and age range of the patients. Such a reporting list of physician activities would help the manufacturer to strategize business planning and maximize return on promotions.

Companies that offer reporting lists of provider activities generally obtain their information from the providers. However, the information from many providers is often summary data of the total number of diagnoses and treatments that the providers have performed. For instance, a hospital provides a summary for its many physicians. Those summaries typically do not provide breakdowns of how many diagnoses and treatments each physician affiliated with the hospital has performed. Thus, to estimate how many diagnoses or procedures each physician performed, the total number of services provided by the hospital is divided by the number of physicians. As a result of this crude apportioning approach, summary reports of physician activities do not accurately reflect the actual number of diagnoses and procedures that each physician actually performed.

However, with privacy concerns and laws limiting the ability of pharmaceutical companies to directly target service providers and patients, there is a need for a system and methods to generate reports of provider activities, derived from a database that includes information obtained from standardized and electronically processed medical claim data linked to each individual provider who performed the diagnoses and procedures, but with the information specifically identifying the individual provider or patient information encrypted to assure privacy and assure compliance with, e.g., HIPAA and all other applicable Federal and State laws and regulations.

SUMMARY OF THE INVENTION

Accordingly, an aspect of the present invention is to provide systems and methods for collecting and providing information from medical claim transactions without information for specifically identifying the particular medical service provider. Another object of the present invention is to correlate medical claim transactions with providers' information without using information that can be used to specifically identify the particular medical service provider (provider identifier).

One embodiment of the present invention provides a system for collecting and providing information from prescription claim transactions without information for specifically identifying the particular medical provider. The system includes a central location and a remote location. The remote location includes a least a source of the medical claim transaction (preferably a plurality of sources are included) that contains a remote processor programmed to encrypt the provider identifier from a medical claim transaction and transmit that encrypted medical claim transaction (medical claim transaction with the provider identifier encrypted) to the central location.

The central location contains a first central database containing provider information and a remote processor for matching and associating the encrypted prescription claim transaction with the medical provider information in the central database. The provider information contains an encrypted provider identifier with other provider information, such as such as geographic location, medical specialty, age, gender, and other demographic attributes. The encryption process at the central location is identical to the encryption process at the remote location so that the same provider obtains the same encrypted identifier.

The central location obtains provider information from public sources, such as the Center for Medicare and Medicaid Services' (CMS) National Provider and Plan Enumeration System (NPPES) database, or the Drug Enforcement Administration's Registration File, or State Licensure databases from the various States. This information typically contains provider names (or any identification information, such as identification number, etc.) and their associated provider information (such as geographic locations and medical specialties). The provider names (or other identifiers) obtained from public sources are then assigned an anonymous practitioner key (APK) and is saved in a second database containing APK cross-referenced to the corresponding provider information. The APK can be, for example, an arbitrary number that is assigned to the particular provider name. In a third database, each APK is cross-referenced to all possible provider identifiers, including name and any identification numbers. The provider identifiers in the third database are then encrypted using the same encryption method as at the remote location. This encrypted data from the third database and the data from the second database are combined to produce the first database which contain all possible encrypted provider identifiers cross-referenced to an APK.

The central processor matches the encrypted provider identifier from the prescription claim transaction with the encrypted provider identifiers in the first database. When there is a match, the information from the medical claim transaction is combined with the provider information and saved in a data warehouse. This saved information can be used to generate reports on provider activities.

Other objects, advantages, and features of the invention will become apparent from the following detailed description, which, taken in conjunction with the annexed drawings, discloses a preferred embodiment of the present invention.

BRIEF DESCRIPTION OF THE DRAWINGS

FIG. 2 is a representative listing of prescription claim transactions.

FIGS. 3A-3B are a listing of the prescription claim transactions of FIG. 2 where the prescriber ID has been encrypted.

FIG. 4 is a representative listing of the key database.

FIG. 5 is a representative listing of the specialty database.

FIGS. 6A-6B are a representative listing of the encrypted database.

FIGS. 7A-7B are a representative listing of the provider file database.

DETAILED DESCRIPTION OF THE PREFERRED EMBODIMENT

The present invention provides systems and methods for collecting and providing information from medical claim transactions without information for specifically identifying the particular medical service provider. In the data of the present invention, provider identifiers are encrypted to protect the anonymity of the medical service provider associated with the medical service data. The encrypted identifier allows for cross-referencing and matching of medical claim transaction information with the provider information, while preserving the anonymity of the individual by encrypting all provider identifiers. As such, the medical service data is "de-identified" by encrypting all information that can be used to directly identify an individual provider. The encrypted identifier is appended to the medical claim transaction and provider information so that the claim transaction and the provide information can be matched and associated by the provider identifier without identifying the particular provider.

As used herein, "provider identifier" is used to indicate information that directly and positively identifies a particular provider. This information includes, but is not limited to, names, certain elements of addresses (except zip codes), Drug Enforcement Agency (DEA) Registration Numbers, State License Numbers, National Provider Identifiers (NPI— the provider identifiers used in CMS' NPPES database), or any other unique identifier that may allow direct identification of the provider. Most common provider identifiers include, but are not limited to, names, State License Number, DEA Registration Number, and/or NPI.

"Provider information," as used herein, refers to information about the provider that cannot be used to specifically identify the provider. This information includes, but is not limited to geographic locations (such as zip codes), medical specialties, age, gender, and other demographic attributes. Here, a provider generally refers to anyone who is licensed or authorized to provide health care, such as a physician, dentist, or nurse practitioner. In a preferred embodiment, the medical service provider is licensed or authorized to provide health care or to issue a prescription for a drug.

Figure 1:
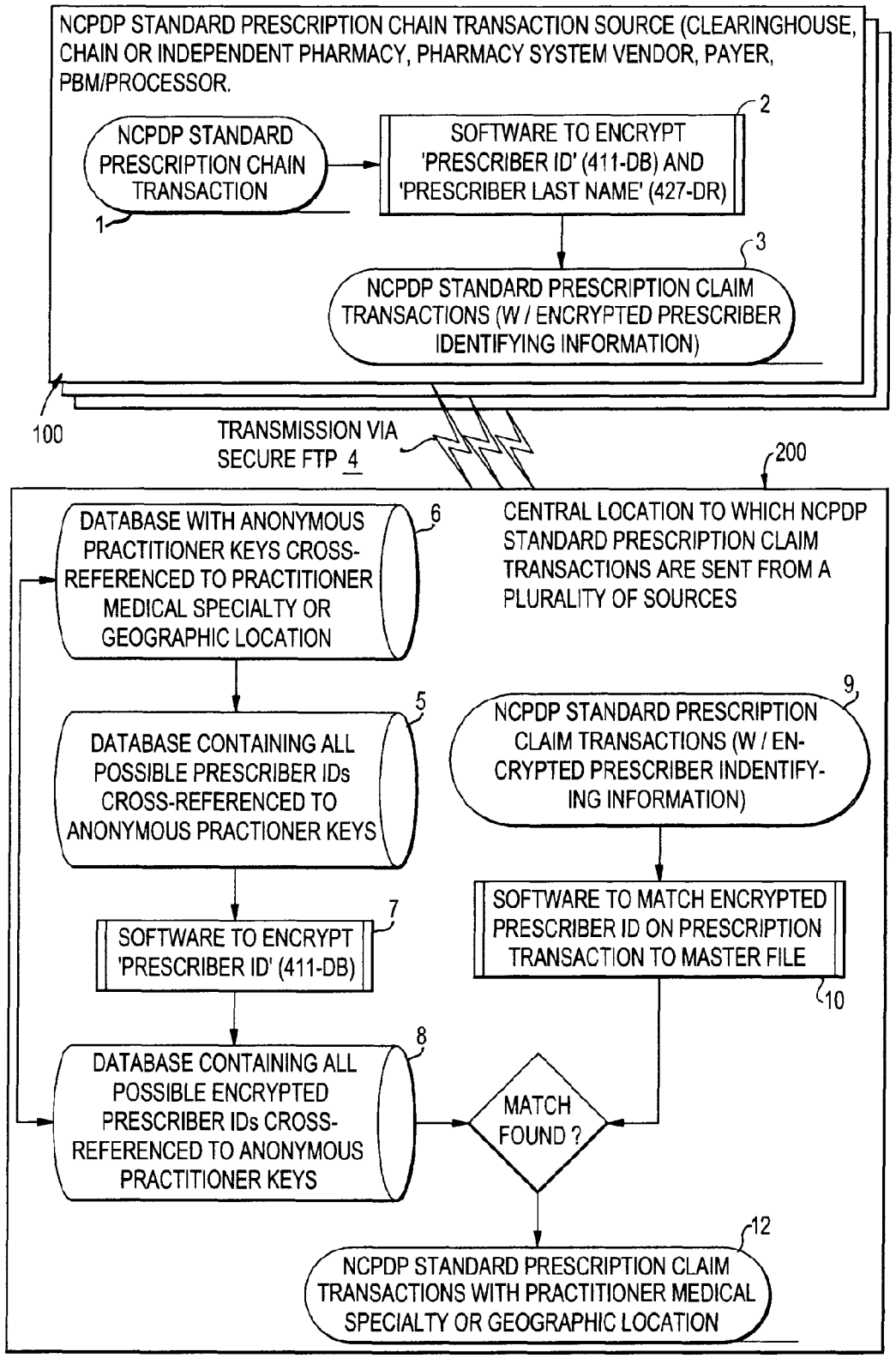
FIG. 1 is a diagram showing the overall process and flow of information in a method of the present invention.

Referring to the FIG. 1, a system is shown having at least a remote location 100 and a central location 200. First, a source (such as for instance a clearinghouse, chain or independent pharmacy, pharmacy system vendor, payer, or PBM/processor) having medical claim transaction information at the remote location 100 includes a database of files having medical claim transaction data 1, which preferably adheres to the NCPDP 5.1 (or later) standard. That transaction data includes at least a provider identifier. For example, a prescription claim transaction (a type of medical claim transaction) under NCPDP 5.1 standard includes prescriber ID (NCPDP data element #411-DB) and/or Prescriber Last Name (NCPDP #427-DR). The data from the medical claim transaction 1 may appear, for example, as shown in FIG. 2, where the prescriber ID is clearly depicted. FIG. 2 shows a sample data set from a prescription claim transaction (a type of a medical claim transaction). Each row of the figure depicts information from a single medical claim transaction, which can include the date of service, the product/service ID, the service provider or pharmacy ID, the prescription /service reference number, and the prescriber ID. Other information from the medical claim transaction may also be included in addition to those depicted in FIG. 2.

Returning to FIG. 1, a processor 2 is provided at each data supplier. The processor 2 receives the medical claim transaction files 1 from the source, and encrypts the provider identifier field(s) (e.g., Prescriber ID (NCPDP #411-DB) and Prescriber Last Name (NCPDP #427-DR) in case of a prescription claim transaction) on each transaction record, using a specific encryption software. The encryption is preferably done by common techniques, such as character substitution or translation, as described in U.S. Pat. No. 4,979,832, which is incorporated herein by reference. The encryption can also be completed by block cipher, hash function, or any other suitable encryption method. A hash function, such as disclosed in U.S. Patent Application Publication No. 2008/0147554, which is incorporated herein by reference, is preferred.

The hash function is a cryptographic primitive. Although another cryptographic primitive, such as a block cipher, can be used, the hash function is preferred because it generally has no inverse function that can recover the input from the hash function's output. The hash function maps a bit string of arbitrary length to another bit string of fixed length. Hash functions include Ripe-MD, Whirlpool, Haval, MD4, MD5, and the SHA group of hash functions. Preferably, the first hash function is from the SHA-2 family, in particular, SHA-256 which creates 256 bit hashes. The SHA family of hash functions was designed by the National Institute of Standards and Technology and is a Federal Information Processing Standard, as described by Federal Information Processing Standards Publication 180-2, dated Aug. 1, 2002. Federal Information Processing Standards Publication 180-2 also provides an algorithm and examples for implementing an SHA-256 hash function.

The processor 2 at the remote location 100 then creates an encrypted medical claim transaction data file 3, which includes the encrypted provider identifier. The original provider identifier data are not included (or NULL'ed out) so that the file cannot be used to specifically identify a provider. For example, using the data of FIG. 2, the prescriber ID is encrypted by the processor 2. The encrypted output is shown in FIGS. 3A-3B, where the prescriber ID has been encrypted and replaced with a character string. Thus, at this point, the medical claim transaction data file 3 contains information in which the provider identifier is encrypted, and thus, the file is de-identified.

The file 3 is then periodically transmitted from the remote location 100 to a central location 200. The transfer is preferably a secured electronic transfer, more preferably via a secure file transfer protocol (sftp). The central location 200 can be remotely located from the data remote locations 100 or at the same location.

A key database 5 is provided at the central location 200. An illustrative example of the data from the key database 5 is shown in FIG. 4. The key database 5 contains all of the identifiers used to identify a particular medical service provider (e.g. a physician). Preferably, the collection is as complete as possible, and more preferably, contains identifiers for all possible medical providers. The identifier(s) for each medical service provider are cross-referenced, in the key database 5, to a unique, anonymous practitioner key (APK). The APK is an internal (to the central location) enumerator assigned to each medical service provider and is preferably available only at the central location 200. Preferably, the APK is a of positive integer (sequential or random). For instance, the key database 5 includes identifiers of medical service providers that can be obtained from public sources, such as name, State License number, DEA number, or NPI (National Provider Identifier) number. The key database 5 links identifier(s) of a particular provider with a single APK. This is particularly useful, because each provider may have multiple identifiers, and can then be identified by a single APK rather than by those identifiers. Of course, the identifier can be used directly, rather than through an APK. In that case, a key database 5 would not be needed; the specialty database 6 (discussed below) would cross-reference provider identifiers directly with provider information; and the encrypted database 7 (discussed below) would encrypt the identifiers in the specialty database 6 rather than the key database 5.

A specialty database 6 is also provided at the central location. The specialty database 6 contains the APKs (referenced with respect to the key database 5 above) cross-referenced to provider information, such as medical specialty and/or geographic location information about each practitioner. This information can be obtained from public sources, such as the CMS NPPES database, the DEA Registration File, and various State Licensure databases. The public sources generally provide the medical service provider information along with identifiers. This information is then parsed to produce the specialty database 6 and the key database 5. An example of the data in the specialty database 6 may appear as shown in FIG. 5. FIG. 5 shows a listing of APKs (first column from the left) and the medical specialties (second and third column from the left) and zip code (furthest right column) for each provider associated with a particular APK. In a preferred embodiment, the specialties are coded, for example, as specified by the American Medical Association (AMA) or the National Plan and Provider Enumeration System (NPPES).

At step 7, the processor 810 (see FIG. 8) deployed at the central location 200, encrypts the identifiers stored in the key database 5. The processor 810 contains the same encryption key as that stored on the processor 2 at the remote location 100. As a result, the same identifier, when encrypted at the central location 200, results in the same character string encryption as when encrypted at the remote location 100. The output from the processor 810 is an encrypted database 8, residing at the central location 200. An example of the data stored in the encrypted database 8 is shown in FIGS. 6A-6B. This encrypted database 8 contains encrypted versions of all possible provider identifiers for each medical service provider cross-referenced to their corresponding APK. Referring to FIGS. 6A-6B, the left column shows a listing of the AKP, while the second column, shows the encrypted identifier (prescriber ID in this case). If more than one identifier is available for additional columns can be added. For example, if a provider has two identifiers, than the listing of the data in the encrypted database would contain three columns, with the first (left) column containing the AKP and the next two columns containing the two identifiers.

A noted above, at step 4, the de-identified file 3 is periodically received at the central location 200 from the remote location 100, preferably via a secure file transfer protocol. The received file 3 contains only an encrypted identifier for each medical service provider, and is stored at the central location 200 as a transaction file 9. At step 10, a processor 810 matches the encrypted identifiers on each prescription claim transaction 9 to the encrypted identifiers stored in the encrypted database 8. If a match is found, the medical service claim transaction associated is then assigned the APK that is associated with the particular identifier from the encrypted database 8. If no successful match is achieved in step 10, then the prescription claim transaction is given a designated APK, for example 0 (zero), indicating that it cannot be linked to any medical service provider information.

With the assigned APK, the processor 810 can associate the medical service provider information from the specialty database 6 with the medical service claim transaction, as shown in FIGS. 7A-7B. This result is then stored in a provider file database 12. Thus, the provider file database 12 contains the medical service claim transactions associated with the encrypted identifiers cross referenced to the medical service provider information. Essentially, the processor 810 uses the APKs and the encrypted identifiers to properly match the provider information from the specialty database 6 with the particular medical service claim transaction. This results in the provider file database 12 containing prescription claim transactions with the encrypted identifiers from transaction file 9 being supplemented with the APKs from the encrypted database 8 and the medical service provider information retrieved from the specialty database 6. The provider information is retrieved from the database 6 based on the anonymous practitioner key corresponding to the encrypted identifier, and that information is joined with the information from transaction file 9. A listing of the data in the provider file database 12 may appear as shown in FIGS. 7A-7B, which matches and supplements the data from the claim transaction data file 3 (first five columns from the left of FIGS. 7A-7B) with the data from the key database 5 (columns 6 to 9 from the left of FIGS. 7A-7B).

Although FIGS. 7A-7B, as an example, shows only the prescriber IDs being encrypted, the methods and systems of the present invention can be used to encrypt other health care provider identifiers listed in the figure, such as pharmacy IDs.

Accordingly, the system allows the at least one remote location 100 to transmit prescription claim transaction data with encrypted identifier(s) to the central location 200.

This encrypted prescription claim transaction data is devoid of any provider identifier. The central location 200 then decrypts that data and fills in provider information obtained from publicly-available sources (as contained in the specialty database 6).

Figure 8:
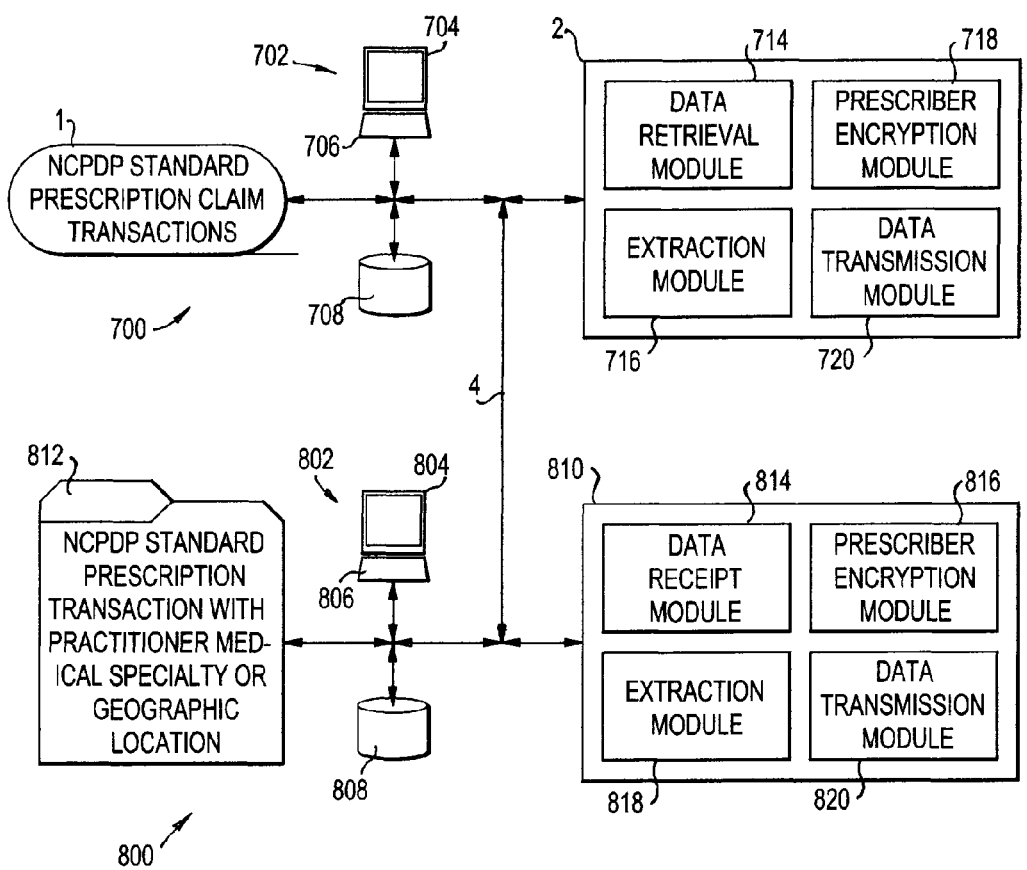
FIG. 8 is a system to carry out the method of the present invention.

It should be noted that although the databases 5, 6, 8 and 12 are illustrated conceptually in FIG. 1 as being separate database, they can actually be one or more physical database. For instance, the information that is stored in the database 5, 6, 8, and 12 can all be stored in a single memory device (as shown in FIG. 8 as storage device 808) accessed by one or more processors. Alternatively, database 5 and 6 can be stored in a first memory device and database 8 and 12 can be stored in a second memory device. Any numbers of physical permutations are within the scope of the present invention.

In addition, the medical claim transaction 1 may contain patient identification information. That information can be removed or the information otherwise de-identified to comply with privacy requirements. The present invention can process the provider information simultaneously with or separately from the processing of the patient information. The processes and systems for de-identifying patient identification information are, for example, disclosed in U.S. Patent Application Publication No. 2008/0147554, which is incorporated herein by reference.

FIGS. 2-7B illustrate one example of the flow of information in accordance with the present invention for a prescription claim transaction (i.e. a medical claim transaction). In FIG. 2, the first record, which shown in a rectangular box for purposes of illustration, in the prescription claim transaction database 1 is for a prescription, having a product/service ID 00093723401, filled on Dec. 25, 2008 by pharmacy number 8138105467 under reference number 6809544. The prescription was written by a doctor or nurse (prescriber) having prescriber ID BM1477974. This prescription claim transaction is encrypted and saved as a transaction data file 3. The stored transaction data file 3 is shown as the first record in FIGS. 3A-3B (in the rectangular box), which contains the same information shown in FIG. 2 for that file, except that the prescriber ID has been encrypted as "aZŒ¬□Ê þ Ýr□YrÈñ75Ý□□□"Â{ ]Ü™Jï¥. "This encrypted prescription claim transaction 3 is then transmitted to the central location 200 (step 4).

Turning to FIG. 4 which shows data contained in the key database 5 which matches APKs with prescriber IDs. From the list, prescriber ID BM1477974 (obtained form the public NPT records) is matched with APK 641424 (shown in rectangular box). In FIG. 5, which shows the data contained in the specialty database 6, the same APK (641424) is matched with an AMA medical specialty code FM and NPPES code 207Q00000X (both for family medicine), and with the zip code (75284) of the prescriber's address (see the rectangular box). The prescriber ID from the key database 5 (FIG. 4) is then encrypted using the same encryption program as that used at the remote location 100. This encryption results in the encrypted database 8 shown in FIGS. 6A-6B where the APK 641424 is associated with encrypted prescriber ID "aZŒ ¬□Êþ Ýr□YrÈñ75Ý□□□"Â{ ]Ü™Ji¥ (see the rectangular box). The processor 810 then matches the encrypted prescription claim transaction 9 that was transmitted to the central location (FIGS. 3A-3B) with the data in the specialty database 6 (FIG. 5) using the encrypted database 8 (FIGS. 6A-6B). Once a match is found for the encrypted prescriber ID "aZŒ ¬□Êþ Ýr□YrÈñ75Ý□□□"Â{ ]Ü™Ji¥, " the APK (641424) is used to access the prescriber's medical specialties and zip code (examples of prescriber information) from FIG. 5, which are then appended to the encrypted prescription claim transaction resulting in a provider file 12. For prescription service reference number 6804554 (first record in FIG. 2), its provider file 12 is shown as the first record in FIGS. 7A-7B (shown in rectangular box). Here, in addition to the product/service ID 00093723401, filling date Dec. 25, 2008, pharmacy number 8138105467, and reference number 6809544, APK 641424, medical specialty codes FM and 207Q00000X, and zip code 75284 are added. Thus, this provider file is de-identified because it shows only the encrypted prescriber ID and not the actual prescriber ID (BM1477924).

A computing platform is provided at each of the remote locations 100 and the central location 200 to perform the various functions and operations in accordance with the invention. The computing platform can be, for instance, a personal computer (PC), server or mainframe computer. The computing platform may also be provided with one or more of a wide variety of components or subsystems including, for example, a processor, co-processor, register, data processing devices and subsystems, wired or wireless communication links, input devices, monitors, memory or storage devices such as one or more database.

The system can be a network configuration or a variety of data communication network environments using software, hardware or a combination of hardware and software to provide the processing functions. All or parts of the system and processes can be implemented by computer-readable media, which has stored thereon machine executable instructions for performing the processes described. Computer readable media may include, for instance, hard disks, floppy disks, and CD-ROM or other forms of computer-readable memory such as read-only memory (ROM) or random-access memory (RAM). The processes of the invention can be implemented in a variety of ways and include other modules, programs, applications, scripts, processes, threads or code sections that interrelate with each other.

An embodiment of the system to carry out the above disclosed method is depicted in FIG. 8. This system contains, at least, a remote system 700, preferably located at the remote location 100, and a central system 800, preferably located at the central location 200. The remote system 700 includes a user interface 702, a database 708, a processor 2, and medical service claim transaction data 1. The remote location 700 can be a physician's office, a hospital, a pharmacy, a laboratory, a health insurer, a consultancy, a claims processor, or any other similar facility where medical service claim transaction data is collected, received, provided, or created.

The user interface 702 is in communication with the database 708 and the processor 2. The user interface 702 can be a desktop, handheld, and/or touch screen computing device or any other display and information input device. It preferably has a display 704 and an input device 706. The display 704 can be any device that presents information to the user. The input device 706 can be any device to electronically enter the medical service claim transaction data 1, such as, but not limited to, a keyboard, touch screen, mouse, scanner, digital camera, or other similar device for transmuting non-electronic information into electronic data.

The database 708 is in communication with the user interface 702 and the processor 2. The database 708 stores medical service claim transaction information data 1. The database 708 can be separate from the processor 2 or can be stored in memory internal to the processor 2. Though a single database 708 is shown in the embodiment of FIG. 1, more than one database can be provided. If more than one database is provided, each separate database is preferably in communication with each other, the user interface 702, the processor 2, or any combination of these components.

The processor 2 is in communication with the user interface 702 and the database 708. The processor 2 preferably has one or more of the following modules: a data retrieval module 714, an extraction module 716, an encryption module 718, and a data transmission module 720. Each of the modules described herein has various sub-routines, procedures, definitional statements, macros, and other similar processes. Software is provided in the processor 2 to implement the operations performed at the remote location 100, including encrypting the provider identifiers and transmitting the encrypted medical service claim transactions. The software includes programming that embodies the data retrieval module 714, which retrieves the medical service claim data from the database 708, if such data is stored in a database; the extraction module 716, which extract the desired data from the medical service claim data; the encryption module 718, which encrypts the provider identifier; and the data transmission module 720, which controls the transmission 4 of the encrypted file 3 to the central location 200. In some embodiments, as illustrated in FIG. 8, the database 708 can be used to store both the medical service claim data 1 and the encrypted file 3 before transmission to the central location. Alternatively, the medical service claim data 1 and the encrypted file 3 can be stored on different databases. In other embodiments, the medical service claim data 1 can be continuously encrypted as it is entered at the user interface 702; and the encrypted file 3 is continuously transmitted to the central location 200. In this case, the remote system 700 may not require a database 708 at all. Similarly, because the database 708 is not required, the data retrieval module 714 and extraction module 716 may also be omitted from the processor 2. The processes that are performed by each of the modules may be redistributed to one of the other modules, combined together in a single module, or made available in a shareable dynamic link library.

A central system 800, located at the central location 200, is also shown in FIG. 8, which includes a user interface 802, a storage device 808, a processor 810, and a combined report 812. The central system 800 can be located near to or remote from the data source (or remote system 700). The user interface 802 is similar to the user interface 702 of the remote system 700, and includes similar display 804 and input device 806.

The storage device 808 is in communication with the user interface 802 and the processor 810. The storage device 808 electronically stores medical service data and include the specialty database 6, the key database 5, and the encrypted database 8. Though a single storage device 808 is shown in the embodiment of FIG. 8, more than one storage device can be provided. For example, if three storage devices are use, each can be dedicated to one of the database. If more than one storage device is provided, each separate storage device is preferably in communication with each other, the user interface 802, the processor 810, or any combination of these components. Also, in other embodiments, the storage device 808 can be the memory associated with the processor 810.

The processor 810 is in communication with the user interface 802 and the storage device 808. The embodiment of FIG. 8 uses only one processor 810 to perform all of the operations of the central location 200, including the functions of steps 7 and 10; however, in other embodiments, the functions of steps 7 and 10 can be separate and implemented by more than one processors. The processor 810 preferably has one or more of the following modules: a data reception module 814, an encryption module 816, an extraction module 818, and a data transmission module 820. Each of the modules described herein has various sub-routines, procedures, definitional statements, macros, and other similar processes. Software is provided in the processor 810 to implement the methods of these modules. The software includes programming that embodies the data receipt module 814, the encryption module 816, the extraction module 818, and the data transmission module 220. The description of each of the modules is used for convenience to describe the functionality of the processor 810 overall. Thus, the processes that are performed by each of the modules may be redistributed to one of the other modules, combined together in a single module, or made available in a shareable dynamic link library.

The modules 814-820 are programmed to carry out functions previously described for steps 7 and 10. The data receipt module 814 receives medical service claim transaction data transmitted from the remote system 700. The extraction module 818 extract data from the various database and compares the encrypted identifiers on each prescription claim transaction to the encrypted identifiers stored in the encrypted database 8 (function of step 10). The encryption module 816, containing the same encryption software as the encryption module 718 of the remote system 700, encrypts the identifiers from the key database 5 to produce the encrypted database 8 (function of step 7). The data transmission module 820 can be used to forward the provider file 812 to a provider file database 12 or to another location.

The user interface 802, the storage device 808, and the processor 810 can each be coupled to the Internet or a network such as a local area network (LAN) or wide area network (WAN). The system is not limited to hard-wired connections but can include wireless communication such as radiofrequency (RF), 802.11 (WiFi), Bluetooth or any combination of data communications paths. For example, the central location 200 can be implemented or incorporated as a single device such as a stand alone computer or a PDA or the storage device 808 can be placed on a remote server coupled to the Internet by hard-wired connections with other components located nearby in wireless communication with the Internet.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A system comprising:
one or more data storage devices storing one or more databases, wherein the one or more databases include:
a specialty database storing anonymous practitioner keys (APKs), each cross-referenced to a medical specialty and a geographic location of a corresponding medical provider; and
an encrypted database storing encrypted medical provider identifiers, each encrypted using a one-way encryption with no inverse function from the one-way encryption and each cross-referenced to an anonymous practitioner key; and
one or more processors configured to:
receive de-identified medical claim transaction data, wherein the received de-identified medical claim transaction data includes one or more encrypted medical provider identifiers that are encrypted using the one-way encryption with no inverse function to recover from the one-way encryption;
match at least one of the received one or more encrypted medical provider identifiers with one or more encrypted medical provider identifiers stored at the encrypted database;
wherein a match is a deterministic match determined by an exact correspondence between at least one of the received one or more encrypted medial provider identifiers and one or more encrypted medical provider identifiers stored at the encrypted database;
identify an APK that is cross-referenced to a matched encrypted medical provider identifier according to the deterministic match;
associate, using the APK that is cross-referenced in the specialty database to a medical specialty and a geographic location of a corresponding medical provider the medical specialty and the geographic location of the medical provider to whom the APK has been assigned and who has provided a service as described by the de-identified medical claim transaction data; and
determining a total number of services provided by the medical provider in the medical specialty and in the geographic location.

2. The system of claim 1, wherein the received one or more encrypted medical provider identifiers each comprise an encrypted name of a medical provider and an encrypted unique identification number of the medical provider.

3. The system of claim 2, wherein the unique identification number of the medical provider is a Drug Enforcement Agency (DEA) Registration Number, a CMS National Provider Identifier (NPI), a State License Number, or any other allowable medical provider identifier.

4. The system of claim 1, wherein the specialty database further stores, age, gender, or other demographic attributes of the medical provider.

5. The system of claim 1, wherein, responsive to a user request for a report of the medical provider's activities, the one or more processors generate the report to identify the total number of services provided by the medical provider.

6. The system of claim 1, wherein the one or more databases further include a key database to store one or more unencrypted medical provider identifiers, each identifying the medical provider and each cross-referenced to the APK that is assigned to the medical provider, and wherein each encrypted medical provider identifier stored in the encrypted database is encrypted by the one or more processors, using the one-way encryption, from a corresponding unencrypted medical provider identifier.

7. The system of claim 1, wherein the one or more processors do not transmit APKs to locations other than a location in the one or more databases.

8. The system of claim 1, wherein, responsive to a user request for a report of activities in a geographic location, the one or more processors generate the report to identify a total number of services provided by all medical providers in the geographic location.

9. The system of claim 1, wherein, responsive to a user request for a report of activities in a medical specialty and in a geographic region, the one or more processors generate the report to identify a total number of services provided by all medical providers of the medical specialty in the geographic location.

10. The method of claim 1, further comprising, responsive to a user request for a report of activities in a geographic location, generating the report to identify a total number of services provided by all medical providers in the geographic location.

11. A computer-assisted method comprising:
receiving, by one or more processors, de-identified medical claim transaction data, wherein the received de-identified medical claim transaction data includes one or more encrypted medical provider identifiers that are encrypted using the one-way encryption with no inverse function to recover from the one-way encryption;
matching at least one of the received one or more encrypted medical provider identifiers with one or more encrypted medical provider identifiers stored at an encrypted database;
wherein a match is a deterministic match determined by an exact correspondence between at least one of the received one or more encrypted medial provider identifiers and one or more encrypted medical provider identifiers stored at the encrypted database;
identifying an APK that is cross-referenced to a matched encrypted medical provider identifier according to the deterministic match;
associating, using the APK that is cross-referenced in a specialty database to a medical specialty and a geographic location of a corresponding medical provider the medical specialty and the geographic location of the medical provider to whom the APK has been assigned and who has provided a service as described by the de-identified medical claim transaction data; and
determining a total number of services provided by the medical provider in the medical specialty and in the geographic location.

12. The method of claim 1, wherein the received one or more encrypted medical provider identifiers each comprise an encrypted name of a medical provider and an encrypted identification unique number of the medical provider.

13. The method of claim 12, wherein the unique identification number of the medical provider is a Drug Enforcement Agency (DEA) Registration Number, a CMS National Provider Identifier (NPI), a State License Number, or any other allowable medical provider identifier.

14. The method of claim 11, wherein the specialty database further stores age, gender, or other demographic attributes of the medical provider.

15. The method of claim 11, further comprising, responsive to a user request for a report of the medical provider's activities, generating the report to identify the total number of services provided by the medical provider.

16. The method of claim 11, wherein the APKs are not transmitted to locations other than a location in the encrypted database and the specialty database.

17. The method of claim 11, further comprising, responsive to a user request for a report of activities in a medical specialty and in a geographic region, the one or more processors generate the report to identify a total number of services provided by all medical providers of the medical specialty in the geographic location.

18. A system comprising;
one or more processors; and
a non-transitory computer-readable medium coupled to the one or more processors having instructions stored thereon which, when executed by the one or more processors, cause the one or more processors to perform operations comprising:
receiving, by the one or more processors, de-identified medical claim transaction data, wherein the received de-identified medical claim transaction data includes one or more encrypted medical provider identifiers that are encrypted using the one-way encryption with no inverse function to recover from the one-way encryption;
matching at least one of the received one or more encrypted medical provider identifiers with one or more encrypted medical provider identifiers stored at an encrypted database;
wherein a match is a deterministic match determined by an exact correspondence between at least one of the received one or more encrypted medial provider identifiers and one or more encrypted medical provider identifiers stored at the encrypted database;
identifying an APK that is cross-referenced to a matched encrypted medical provider identifier according to the deterministic match;
associating, using the APK that is cross-referenced in a specialty database to a medical specialty and a geographic location of a corresponding medical provider the medical specialty and the geographic location of the medical provider to whom the APK has been assigned and who has provided a service as described by the de-identified medical claim transaction data; and
determining a total number of services provided by the medical provider in the medical specialty and in the geographic location.

19. A non-transitory computer-readable medium encoded with instructions that, when executed by one or more processors, cause the one or more processors to perform operations comprising:
receiving de-identified medical claim transaction data, wherein the received de-identified medical claim transaction data includes one or more encrypted medical provider identifiers that are encrypted using the one-way encryption with no inverse function to recover from the one-way encryption;
matching at least one of the received one or more encrypted medical provider identifiers with one or more encrypted medical provider identifiers stored at an encrypted database;
wherein a match is a deterministic match determined by an exact correspondence between at least one of the received one or more encrypted medial provider identifiers and one or more encrypted medical provider identifiers stored at the encrypted database;

identifying an APK that is cross-referenced to a matched encrypted medical provider identifier according to the deterministic match;

associating, using the APK that is cross-referenced in a specialty database to a medical specialty and a geographic location of a corresponding medical provider the medical specialty and the geographic location of the medical provider to whom the APK has been assigned and who has provided a service as described by the de-identified medical claim transaction data; and determining a total number of services provided by the medical provider in the medical specialty and in the geographic location.

\* \* \* \* \*